(12) United States Patent
Memar

(10) Patent No.: US 7,771,754 B2
(45) Date of Patent: Aug. 10, 2010

(54) APPARATUS AND METHODS FOR REPAIRING TISSUE DEFECTS

(76) Inventor: Omeed Memar, Suite 720, Chicago, IL (US) 60602

( * ) Notice: Subject to any disclaimer, the term of this patent is extended or adjusted under 35 U.S.C. 154(b) by 232 days.

(21) Appl. No.: 11/531,930

(22) Filed: Sep. 14, 2006

(65) Prior Publication Data

US 2008/0121745 A1    May 29, 2008

(51) Int. Cl.
*A61K 35/32* (2006.01)
*A61K 35/36* (2006.01)

(52) U.S. Cl. ...................... 424/574; 424/93.7

(58) Field of Classification Search ....................... None
See application file for complete search history.

(56) References Cited

U.S. PATENT DOCUMENTS 5,424,208 A * 6/1995 Lee et al. .................... 435/268

FOREIGN PATENT DOCUMENTS

WO    WO 02/088296 A1 * 11/2002

OTHER PUBLICATIONS

Alster et al., Plastic & Reconstructive surgery, 2000, vol. 105, No. 7, p. 2515-2525.*
Sclafani et al., Arch Facial Plast Surg, 2000, vol. 2, p. 130-136.*
Pulverized, Definition from the Merriam-Webster Online Dictionary.*
Grinding, Definition from the Merriam-Webster Online Dictionary.*
Homogenized, Definition from the Merriam-Webster Online Dictionary.*

* cited by examiner

*Primary Examiner*—L Blaine Lankford
*Assistant Examiner*—Kade Ariani
(74) *Attorney, Agent, or Firm*—Mark J. Nahnsen; Barnes & Thornburg LLP

(57) ABSTRACT

Methods and devices to process harvested skin tissue and reintroduction of the ground tissue to repair a tissue defect are disclosed. A hand-held portable tissue grinder comprising a housing and a grinding element are disclosed. The tissue grinder is used for grinding skin and subcutaneous tissue and includes a sterile polymer housing having a first opening adapted to receive the skin and subcutaneous tissue and a second opening in fluid connection with the first opening. The tissue grinder also includes a sterile grinding element disposed substantially within the housing. The grinding element includes a plurality of cutting surfaces adapted to operably engage with the housing to provide ground tissue and further includes a handle mechanism coupled to the grinding element to move the grinding element with respect to the housing to grind the skin and subcutaneous tissue, wherein the ground tissue can be removed from the housing through the second opening.

12 Claims, 1 Drawing Sheet

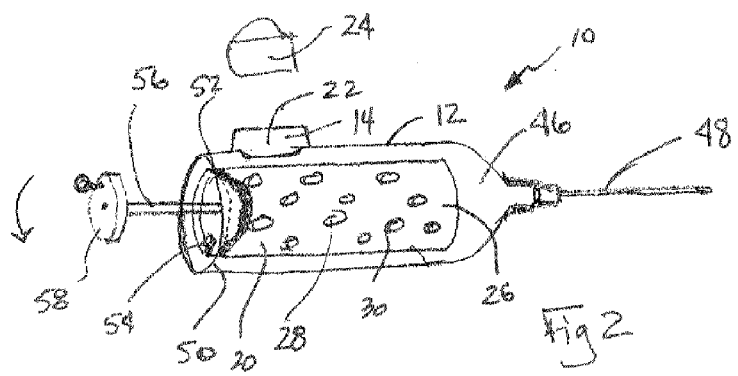
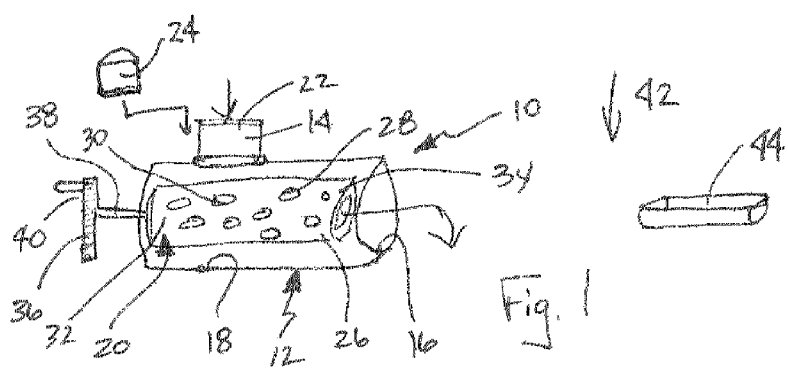
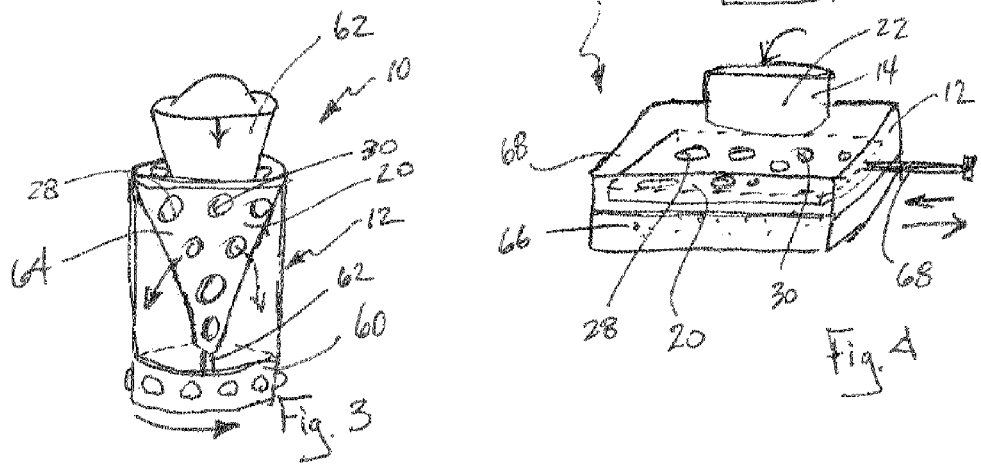
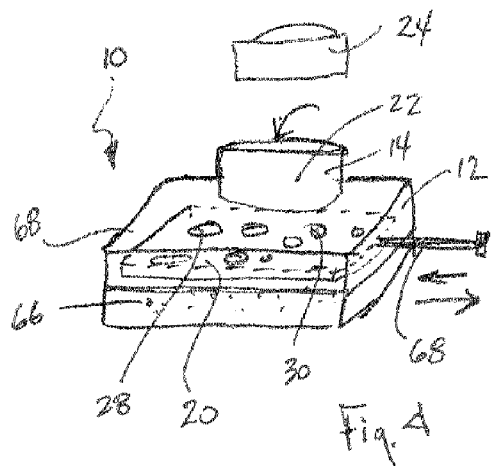

APPARATUS AND METHODS FOR REPAIRING TISSUE DEFECTS

FIELD

The present disclosure generally relates to devices and methods for repairing tissue defects. More particularly, the present disclosure relates to processing of harvested skin tissue, processing the skin tissue, reintroducing the processed skin tissue to a defective site, and repairing the defect.

BACKGROUND

Skin tissue generally comprises three distinct layers including the epidermis, the dermis, and the hypodermis or the sub-cutaneous layer.

The epidermis is the surface layer of the skin tissue and the thickness of the epidermis depends on a number of factors, including age, sex and the location on the body. For example, the skin on the bottom of the foot can be up to 30 cell-layers thick, while the skin on the eyelids is extremely thin. About 90 percent of the cells in the epidermis are keratinocytes, designated because they produce a characteristic fibrous protein called keratin, which provides many of the skin's protective properties. The bottom section of the epidermis, called the basal layer, contains melanocytes, which produce melanin—the skin pigment.

The dermis layer is positioned immediately beneath the epidermis and is connected by a continuous membrane. The dermis forms the thickest section of skin tissue and contains blood vessels, white blood cells, nerve endings, hair follicles, sweat glands and sebaceous glands. Fibroblasts constitute the main cell type in the dermis and they provide a source for collagen and elastin, the fibrous proteins that form the primary structural components of the skin tissue. The dermis provides moisture to the epidermis, produces collagen and elastin to maintain the structural integrity of the skin tissue, and generates sebum to keep the skin supple and hydrated.

The hypodermis or the sub-cutaneous layer beneath the dermis, is composed of an extensive network of connective tissue and is imbued with fat cells. It acts as a protective cushion and helps to insulate the body by monitoring heat gain and heat loss. The sub-cutaneous or the hypodermis layer is some times not considered as part of the skin tissue.

Correction of tissue defects including functional, cosmetic, and aesthetic defects have primarily focused on injecting or implanting non-biological materials such as saline and silicone or processed biological materials such as isolated and cultured fibroblasts or other tissue cells. Introducing non-biological material or biological material derived from another source, for example, bovine collagen or cultured fibroblasts, may result in adverse reactions in the individual. The adverse reactions include local or systemic irritation, and inflammation. Collagen, cartilage material, and bone tissue have also been used to strengthen the bone tissue or the tissue surrounding bone tissue. Some tissue engineering techniques involve culturing of isolated cells in vitro prior to implantation.

Therefore, there exists a need for simpler and practical procedures to repair tissue defects, including skin defects and for a device to process the tissue to enable repairing the defective tissue. The present disclosure provides methods to process a suitable tissue using a tissue grinder and to reintroduce the processed tissue to correct or repair the defective tissue site.

SUMMARY

According to the present disclosure, a tissue grinder is used to process a suitable tissue from a suitable source such that the processed tissue is amenable for reintroduction to a defective site for repairing the defect. A suitable tissue is for example, a skin tissue and a suitable source, for example, is an abdominal area.

The method of repairing a defective tissue site includes the steps of obtaining a skin and subcutaneous tissue from a suitable source, removing a top epithelial component from the skin and the subcutaneous tissue and grinding the skin and subcutaneous tissue into constituents in a tissue grinder to provide a ground tissue, the tissue grinder comprising a cutting surface. The method also includes reintroducing the ground tissue to the defective site by directly applying the ground tissue at the defective site to repair the defective site.

The method incorporates the use of a surgical hand-held tissue grinder. The tissue grinder is used for grinding skin and subcutaneous tissue and includes a sterile polymer housing having a first opening adapted to receive the skin and subcutaneous tissue and a second opening in fluid connection with the first opening. The tissue grinder also includes a sterile grinding element disposed substantially within the housing. The grinding element includes a plurality of cutting surfaces adapted to operably engage with the housing to provide ground tissue and further includes a handle mechanism coupled to the grinding element to move the grinding element with respect to the housing to grind the skin and subcutaneous tissue, wherein the ground tissue can be removed from the housing through the second opening.

Additional features of the present disclosure will become apparent to those skilled in the art upon consideration of the following detailed description of illustrative embodiments exemplifying the best mode of carrying out the disclosure as presently perceived.

BRIEF DESCRIPTION OF THE DRAWINGS

The present invention and the advantages thereof will become more apparent upon consideration of the following detailed description when taken in conjunction with the accompanying drawings of which:

FIG. 1 is a perspective view of an embodiment of a hand-held tissue grinder illustrating a grinding element and a housing in accordance with the present disclosure;

FIG. 2 is a perspective view of an embodiment of a hand-held tissue grinder illustrating a grinding element and a housing in accordance with the present disclosure; and FIG. 3. is a perspective view of an embodiment of a hand-held tissue grinder illustrating a grinding element and a housing in accordance with the present disclosure, wherein the tissue grinder is adapted to introduce the processed skin tissue to a defective site.

FIG. 4 is a perspective view of a reciprocating type tissue grinder.

DETAILED DESCRIPTION

While the present disclosure may be susceptible to embodiment in different forms, there are shown in the drawings, and herein will be described in detail, embodiments with the understanding that the present description is to be considered an exemplification of the principles of the disclosure and is not intended to limit the disclosure to the details of construction and the arrangements of components set forth in the following description or illustrated in the drawings.

The disposable, surgical hand-held tissue grinder 10 is adapted for grinding skin and subcutaneous tissue for use in repairing tissue defects. The tissue grinder 10, as is shown in FIG. 2, includes a sterile polymer housing 12 having an inlet 14 and an outlet 16. The housing 12 includes a cylindrical bore 18 that extends through housing 12. Bore 18 is adapted to accept a sterile grinding element 20 disposed within the bore 18. The tolerances between the grinding element 20 and bore 18 are such that grinding element is in contact with housing 12.

The housing 12 is dimensioned to fit within the hand of a medical practitioner to make it easy to operate the tissue grinder 10 during the medical procedure. Housing 12 is sterilized and is ready to be used by the medical practitioner from the packaging and can be discarded after the procedure is completed. Inlet 14 of housing 12 includes cylindrical wall 22 that is in fluid communication with bore 18. Cylindrical wall 22 is adapted to contain excised tissue prior to grinding. In order to force the tissue through inlet 14 onto grinding element 20, a plug 24 is used to force the tissue into bore 18. Housing 12 is preferably made from a polymer material so that it can be disposed of after use.

Sterile grinding element 20 is disposed substantially within housing 12. Sterile grinding element 20 is preferably cylindrical and includes a cylindrical wall 26. The diameter of cylindrical wall 26 is less than the diameter of cylindrical wall 92 such that cylindrical wall 26 can rotate with respect to cylindrical wall 22 of housing 12. Grinding element 20 also includes a plurality of openings 28 that include cutting surfaces 30 in the form of sharpened edges at the edge of openings 28. Grinding element 20 includes a first end 32 and a spaced apart second end 34. First end 32 of grinding element 20 is connected to handle 36 which is used to rotate grinding element 20 with respect to housing 12. Handle 36 includes shaft 38 that is connected to grinding element 20 and end member 40 which is connected to shaft 38. Rotation of handle 36 causes rotation of grinding element 20 inside of housing 12. When tissue positioned within inlet 14 is forced downward in direction 42 cutting edges 30 of grinding element 20 engage and cut tissue which is then deposited through openings 28 into the center of grinding element 20. Cut tissue that passes through openings 28 and collects within grinding element 20 either settles in tray 44 or passes through second end 34 of grinding element 20 when tissue grinder 10 is tilted. Tissue grinder 10 may also include a closed end 46 that includes a hypodermic needle 48. Housing 12, shown in the illustrative embodiment of FIG. 2, includes an open end 50 that is adapted to accept plunger 52. Plunger 52 is adapted to fit within cylindrical wall 26 of grinding element 20. Plunger 52 includes locking tab 54 and is adapted to lock plunger 52 with respect to grinding element 20. Plunger 52 is connected to shaft 56, which in turn is connected to handle 58. Rotation of handle 58 causes rotation of shaft 56, plunger 52 and cylindrical wall 26 so that tissue inserted into inlet 14 is ground by cutting edges 30 of openings 28. Tissue cut by cutting edges 30 collects within cylindrical wall 26 of grinding element 20. When the desired amount of tissue has been collected, handle 58 is depressed towards open end 50 to move plunger 52 through the cylindrical wall 26 of grinding element 20. This forces minced tissue to closed end 46 and ultimately through hypodermic needle 43 for injection.

Another method for mincing or grinding tissue is shown in the illustrative embodiment of FIG. 3 wherein housing 12 contains conically shaped grinding element 20. Grinding element 20 includes opening 28 that have cutting faces 30 to grind or mince tissue. Grinding element 20 is rotated with respect to housing 12 by use of rotary knob 60. Knob 60 is connected to grinding element 20 by use of shaft 62. Also used is a conical plug 62 that is adapted to force tissue against conical wall 64 of tissue grinder 10 so that tissue engages cutting edges 30 of openings 28. Ground tissue is collected in knob 60 for use in reintroducing the processed skin tissue into a defective site.

Tissue grinder 10 may also be of the reciprocating type as shown, for example, in the illustrative embodiment of FIG. 4. Tissue grinder 10 includes housing 12 having an upper half 68 and a lower half 66. Disposed within the housing 12 is a grinding element 20 that includes a plurality of openings 28 having cutting edges 30. Grinding element 20 is moved in a reciprocating fashion with respect to housing 12 by use of handle 68. Tissue to be ground is placed into inlet 14 formed by cylindrical wall 22. Tissue that has been placed within inlet 14 is forced against grinding element 20 by use of plug 24. Tissue ground by cutting edges 30 of openings 28 is collected in lower half 66 of sterilized housing 12. Collected tissue is then reintroduced to a defective site by use of a syringe or other means.

In an embodiment, a suitable tissue such as, for example, a skin and subcutaneous tissue is obtained from a suitable source of an individual with a tissue defect. As used herein, "skin and subcutaneous tissue" generally refers to the skin tissue comprising the epidermis, the dermis and the hypodermis or the layer beneath the dermis layer. In addition, the term "skin tissue" generally refers to the epidermal and the dermal layers. For example, a suitable source to obtain the skin and subcutaneous tissue is lower abdominal area. Other suitable sources include thigh, buttocks, and any bodily region capable of providing an adequate amount of the skin and subcutaneous tissue.

Any tissue that can be ground and reintroduced to repair a tissue defect or augment the structural or functional integrity of a tissue is within the scope of this disclosure.

The skin and subcutaneous tissue is removed from the suitable source by employing any suitable technique that is practiced in the art. For example, the skin and subcutaneous tissue is obtained from the abdominal region by surgically excising the desired tissue from the source. The nature and the amount of the tissue depends on the nature of the defect and the extent of the defect to be repaired and the availability of suitable tissue at the source. For example, a tissue defect includes a facial defect. The tissue defect can be functional, cosmetic or a combination thereof. Some examples of tissue defects includes, for example wrinkles, altering of facial contours and scar correction. It is preferable to obtain the tissue from the same individual for whom the tissue defect is corrected.

In an embodiment, after the tissue is obtained from the suitable source, the skin tissue is processed by removing an epithelial component or the epidermal layer of the skin tissue. Epithelial components include, such as, for example, keratinocytes, dendritic cells, melanocytes, hair follicles and squamous cell. It is preferable to substantially remove the hair follicles and other undesirable constituents prior to reintroduction of the ground tissue to the defective tissue site. The epithelial component is removed using any standard methods available in the art. For example, an epithelial component is removed by mechanical force, Other modes of removal, such as, for example, chemical and biological treatments can also be used to remove or substantially reduce the prevalence of an epithelial component in the harvested skin and subcutaneous tissue.

After an appropriate amount of the skin and subcutaneous tissue has been processed, the processed tissue is subject to a grinding force in a tissue grinder. In an embodiment, the grinding force is a torque applied by a grinding element of the grinder. In an embodiment, the grinding element includes cutting surface that has a plurality of openings. Other forms of mechanical action, in addition to the rotational torque is suitable. For example, horizontal sliding movement of the grinding element is also suitable for operating the tissue grinder to provide a ground tissue. Briefly, the harvested tissue is transferred to the tissue grinder through an opening in the housing of the grinder. Optionally, the tissue is held against the grinding element by force such that the grinding element engagedly contacts the tissue. The grinding element is operated such that the movement of the grinding element with respect to the housing grinds the tissue. The ground tissue is collected and transferred to another suitable device, e.g., a syringe to be introduced into the defective tissue site.

In an embodiment the skin and subcutaneous tissue is ground by the grinder such that the ground tissue has constituents that range in size from about 50 μm to about 5000 μm in diameter. The constituents can also range in size from about 100 μm to about 1000 μm; and from about 500 μm to about 3000 μm. The ground tissue includes skin constituents that range in size that are slightly bigger than the size of an individual cell to about 10-100 times bigger than the size of the individual cell. The ground skin and subcutaneous tissue contains aggregates of cells that are capable of providing support for growth and establishment of the implanted tissue and correct the tissue defect. For example, fat cells and blood vessels that form a part of the dermal layer and the subcutaneous layer provide nourishment to support the growth of the skin tissue fat immediately surrounds the implanted tissue.

After the tissue is ground, optionally the tissue is transferred to a suitable applicator device, such as, for example, a syringe. The ground tissue is then directly administered at a defective site. In an embodiment, the ground tissue is injected or applied beneath the existing skin and subcutaneous tissue to correct the defect. The ground tissue can be applied under or over any layer as long as the implanted ground tissue (graft) is accepted by the surrounding tissue (host). The ground tissue can also be applied directly on a defective site with any suitable applicator. An incision can be made at the defective site to permit effective implantation of the ground tissue. After the implantation, appropriate surgical measures, such as, suturing and bandaging the defective site, are adopted as necessary.

In another embodiment, the tissue grinder is adapted to functionally engage the applicator device so that the tissue removal and transfer step is eliminated. In yet another embodiment, the tissue grinder itself comprises an applicator member capable of transferring the ground tissue to the defective site.

While embodiments have been illustrated and described in the drawings and foregoing description, such illustrations and descriptions are considered to be exemplary and not restrictive in character, it being understood that only illustrative embodiments have been shown and described and that all changes and modifications that come within the spirit of the invention are desired to be protected. The applicants have provided description and figures which are intended as illustrations of embodiments of the disclosure, and are not intended to be construed as containing or implying limitation of the disclosure to those embodiments. There are a plurality of advantages of the present disclosure arising from various features set forth in the description. It will be noted that alternative embodiments of the disclosure may not include all of the features described yet still benefit from at least some of the advantages of such features. Those of ordinary skill in the art may readily devise their own implementations of the disclosure and associated methods, without undue experimentation, that incorporate one or more of the features of the disclosure and fall within the spirit and scope of the present disclosure and the appended claims.

What is claimed is:

1. A method of repairing a defective tissue site on the individual, the method comprising the steps of:
    (a) obtaining skin tissue from a suitable site on the individual, wherein the tissue is epidermis, dermis and hypodermis;
    (b) removing epithelial components from the skin tissue;
    (c) grinding the tissue that remains from step b) in a tissue grinder to provide a ground tissue, the tissue grinder comprising a cutting surface; and
    (d) reintroducing the ground tissue to the defective site by applying the ground tissue from (c) directly at the defective site and thereby repairing the defective site.

2. The method of claim 1, wherein the tissue in step c) is ground into particles having a size of about 50 μm to about 5000 μm in diameter.

3. The method of claim 1, wherein the defect is a facial defect.

4. The method of claim 1, wherein the skin tissue is obtained from the source by skin excision.

5. The method of claim 1, wherein the epithelial components are removed by mechanical force.

6. The method of claim 1, wherein the tissue grinder comprises a housing and a grinding element, the grinding element comprising a plurality of openings such that the operation of the grinding element in conjunction with the housing results in the ground tissue.

7. The method of claim 1, wherein the ground tissue is administered by a syringe.

8. The method of claim 7, wherein the syringe is adaptably connected to the tissue grinder.

9. The method of claim 1, wherein the tissue grinder is functionally adapted to transfer the ground tissue into the defective site.

10. The method of claim 1, wherein the tissue grinder is disposable.

11. The method of claim 1, wherein the tissue grinder is sterilizable.

12. The method of claim 1, wherein the tissue grinder is hand-held.

* * * * *